(12) United States Patent
Kim et al.

(10) Patent No.: US 10,206,597 B2
(45) Date of Patent: Feb. 19, 2019

(54) NEURAL PROBE ARRAY OF HIGH PERFORMANCE AND FOR MINIMIZED DAMAGE OF NEURON

(71) Applicant: Korea Institute of Science and Technology, Seoul (KR)

(72) Inventors: Jinseok Kim, Seoul (KR); Jong Woong Park, Seoul (KR); Jinwoo Jeong, Seoul (KR); Inchan Youn, Seoul (KR); Ockchul Kim, Seoul (KR); Sang Rok Oh, Gangneung-si (KR); Keehoon Kim, Seoul (KR); Jun Uk Chu, Daegu (KR)

(73) Assignee: Korea Institute of Science and Technology, Seoul (KR)

( * ) Notice: Subject to any disclaimer, the term of this patent is extended or adjusted under 35 U.S.C. 154(b) by 350 days.

(21) Appl. No.: 15/077,172

(22) Filed: Mar. 22, 2016

(65) Prior Publication Data

US 2017/0020403 A1  Jan. 26, 2017

(30) Foreign Application Priority Data

Jul. 24, 2015 (KR) .......................... 10-2015-0105248

(51) Int. Cl.
*A61B 5/04* (2006.01)
*A61B 5/00* (2006.01)

(52) U.S. Cl.
CPC ........ *A61B 5/04001* (2013.01); *A61B 5/4041* (2013.01)

(58) Field of Classification Search
CPC . A61B 5/04001; A61N 1/0551; A61N 1/0556

USPC .......................................... 600/377; 607/118
See application file for complete search history.

(56) References Cited

U.S. PATENT DOCUMENTS

| 4,573,481 | A | * | 3/1986 | Bullara | ................ | A61N 1/0556 |
| | | | | | | 607/118 |
| 4,590,946 | A | * | 5/1986 | Loeb | .................... | A61N 1/0558 |
| | | | | | | 600/375 |
| 4,920,979 | A | * | 5/1990 | Bullara | ................ | A61N 1/0556 |
| | | | | | | 607/118 |
| 4,979,511 | A | * | 12/1990 | Terry, Jr. | ................ | A61B 5/042 |
| | | | | | | 600/377 |
| 5,400,784 | A | * | 3/1995 | Durand | ................ | A61N 1/0556 |
| | | | | | | 29/825 |
| 8,423,143 | B2 | | 4/2013 | Bartic et al. | | |
| 8,639,312 | B2 | * | 1/2014 | Clark | .................... | A61N 1/0556 |
| | | | | | | 600/373 |
| 9,095,267 | B2 | * | 8/2015 | Halpern | ............... | A61B 5/0478 |

(Continued)

FOREIGN PATENT DOCUMENTS

JP  2001-523993 A  11/2001
JP  5041584 B2  7/2012

(Continued)

*Primary Examiner* — Lee S Cohen
(74) *Attorney, Agent, or Firm* — NSIP Law (57) ABSTRACT

A nerve probe array has a connector made of a flexible material; and a plurality of probes coupled to the connector, each of the plurality of probe having an electrode formed at a body thereof. The plurality of probes are arranged with intervals in a length direction of the connector, and the connector surrounds an outer circumference of a nerve, and the plurality of probes pierce the outer circumference of the nerve and are inserted into the nerve.

15 Claims, 11 Drawing Sheets

(56) References Cited

U.S. PATENT DOCUMENTS

| | | | | |
|---|---|---|---|---|
| 2004/0111139 A1* | 6/2004 | McCreery | ............ | A61N 1/0556 |
| | | | | 607/117 |
| 2008/0027524 A1* | 1/2008 | Maschino | ............ | A61N 1/0551 |
| | | | | 607/118 |
| 2012/0022617 A1 | 1/2012 | Tockman et al. | | |
| 2014/0228738 A1 | 8/2014 | Park et al. | | |
| 2014/0288458 A1 | 9/2014 | Yoon et al. | | |
| 2016/0331326 A1* | 11/2016 | Xiang | .................. | A61B 5/6877 |

FOREIGN PATENT DOCUMENTS

| | | | |
|---|---|---|---|
| KR | 10-1158775 B1 | | 6/2012 |
| KR | 10-2012-0084903 A | | 7/2012 |
| KR | 10-2014-0133202 A | | 11/2014 |
| WO | WO 98/46124 | | 10/1998 |
| WO | WO 2013/111985 A1 | | 8/2013 |
| WO | WO2016/005400 | * | 1/2016 |
| WO | WO2016/130812 | * | 8/2016 |

* cited by examiner

NEURAL PROBE ARRAY OF HIGH PERFORMANCE AND FOR MINIMIZED DAMAGE OF NEURON

CROSS-REFERENCE TO RELATED APPLICATION

This application claims priority to Korean Patent Application No. 10-2015-0105248, filed on Jul. 24, 2015, and all the benefits accruing therefrom under 35 U.S.C. § 119, the contents of which in its entirety are herein incorporated by reference.

BACKGROUND

1. Field

The present disclosure relates to a nerve probe array, and more particularly, to a nerve electrode structure connected to a nerve to collect nerve signals through an electrode formed at a probe or apply an electrical stimulation to the nerve.

[Description about National Research and Development Support]

This study was supported by the High-Tech Convergence Technology Development program of Ministry of Science, ICT and Future Planning, Republic of Korea (Project No. 1711015332) under the superintendence of National Research Foundation of Korea.

2. Description of the Related Art

Recently, as a nerve interface used for neuroprosthetics or human-machine interface (HMI), a subminiature nerve electrode structure directly connected to a nerve to apply stimulation to the nerve or collect nerve signal information from the nerve has been studied.

As an example of the subminiature nerve electrode structure, a cuff electrode composed of a body having a broad area and made of a flexible material and an electrode embedded in the body is used.

In the cuff electrode, a flexible body is wound around the entire surface of a nerve like bandaging and is fixed thereto, and a nerve signal is detected through an electrode formed at the surface of the body.

However, the body of the cuff electrode is fixed to perfectly surround the outer circumference of the nerve bundle and thus press a part of the nerve bundle, which may disturb blood circulation in a blood vessel present at the nerve eqineurium and thus cause chronic pain. In addition, the body made of a polymer material does not allow oxygen, water or the like to pass therethrough, which may cause a pain or nerve necrosis at a portion where the body is applied. Therefore, long-term transplantation into the nerve is not easy.

Moreover, since the electrode collects nerve signals at a location out of the nerve bundle, a signal inside the nerve may not be properly read, and signals in the nerve fiber level may not be selectively obtained. Therefore, in case of the cuff electrode, the number of electrodes embedded is generally limited, which may be a factor for limiting applications of neuroprosthetics or HMI.

In order to supplement the problems of an extraneural electrode such as the cuff electrode, an intra-fascicular electrode in which an electrode body is directly inserted into a nerve may be used.

Representatively, there may be used a so-called transverse intra-fascicular multichannel electrode/longitudinal intra-fascicular electrode (TIME/LIFE) for inserting a thread-type electrode body into a nerve bundle to read a nerve signal, a Utah probe electrode having a plurality of probes arranged vertically at a plate-shaped body to put the probes into a corresponding nerve portion, a sieve electrode having a body having a thin plate shape, which may be inserted into a section of a partially cut nerve, so that the body has a hole through which a nerve bundle may pass and an electrode is arranged in the hole, or the like.

However, in case of the TIME/LIFE, it is not easy to position the electrode at a desired location in a nerve, and thus nerve selectivity is low. In addition, since the electrode may not be easily fixed after transplantation, the location of the electrode may be easily varied due to an external force, which is disadvantageous for long-term transplantation.

In case of the Utah electrode, many probes are inserted in a vertical direction of a nerve bundle with large intervals, which results in great redundant damage of neuron. In the fabrication process of the electrode, the material of the probe is limited to hard silicon, which may cause damage of neuron in the long term, and thus the nerve signal acquisition performance may deteriorate.

In addition, in case of the sieve electrode, due to excellent nerve selectivity, when a plurality of electrodes is embedded, a nerve signal corresponding to each electrode may be accurately mapped, but the nerve need to be cut, which results in very serious invasiveness to the nerve.

SUMMARY

The present disclosure is directed to providing a nerve probe array, which may be transplanted to a nerve by minimizing damage and pressure of the nerve, and also allow nerve signals in the nerve to be consistently obtained with high density.

In one aspect, there is provided a nerve probe array, comprising: a connector made of a flexible material; and a plurality of probes coupled to the connector, each of the plurality of probes having an electrode formed at a body thereof, wherein the plurality of probes are arranged with intervals in a length direction of the connector, and wherein the connector surrounds an outer circumference of a nerve, and the plurality of probes pierce the outer circumference of the nerve and are inserted into the nerve.

According to an embodiment, the plurality of probes may include a probe having a different length from another probe.

According to an embodiment, at least one of the plurality of probes may be formed to reach a center of the nerve.

According to an embodiment, when the nerve is observed in a section direction which is perpendicular to the length direction of the connector, the plurality of probes inserted into the nerve may be arranged radially.

According to an embodiment, the plurality of probes may be arranged at regular intervals.

According to an embodiment, the connector may surround the outer circumference of the nerve, so that the plurality of probes are inserted into the nerve at different locations along the length direction of the nerve.

According to an embodiment, the connector may be flexibly bent with an arc shape.

According to an embodiment, the connector may have a linear shape and be length-adjustable along the length direction of the connector.

According to an embodiment, the connector may include: a plurality of fixing portions fixed to the plurality of probes, respectively; and a length-adjustable extendable portion configured to connect fixing portions adjacent to each other.

According to an embodiment, the plurality of probes may be arranged over the entire length of the connector, and the connector may make at least one turn around the nerve.

According to an embodiment, the connector may have a thin plate shape whose width is greater than thickness, and the connector may surround the nerve in a state of erecting so that one side of the connector forming the thickness comes into contact with the outer circumference of the nerve.

According to an embodiment, a plurality of electrodes may be formed at a single probe, and the plurality of electrodes may be formed at different locations along a length direction of the probe.

According to an embodiment, the probe may include a hook structure so that the probe is hooked at the inside of the nerve and is not drawn in a direction opposite to the insertion direction of the probe into the nerve.

According to an embodiment, the hook structure may be a sharp protrusion formed at a side of the probe so that an end of the probe extends in the direction opposite to the insertion direction of the probe into the nerve.

According to an embodiment, a single probe may include a plurality of protrusions, the plurality of protrusions may be formed at different locations along the length direction of the probe, and the plurality of electrodes may be formed to cover the plurality of protrusions, respectively.

According to an embodiment, the plurality of probes may be made of a flexible material or coated with a flexible material at a surface thereof.

DETAILED DESCRIPTION

Hereinafter, an embodiment of the present disclosure will be described with reference to the drawings. Even though the present disclosure is described based on the embodiment depicted in the drawings, thus is just an example, and the essential configuration and operations of the present disclosure are not limited thereto.

Figure 1:
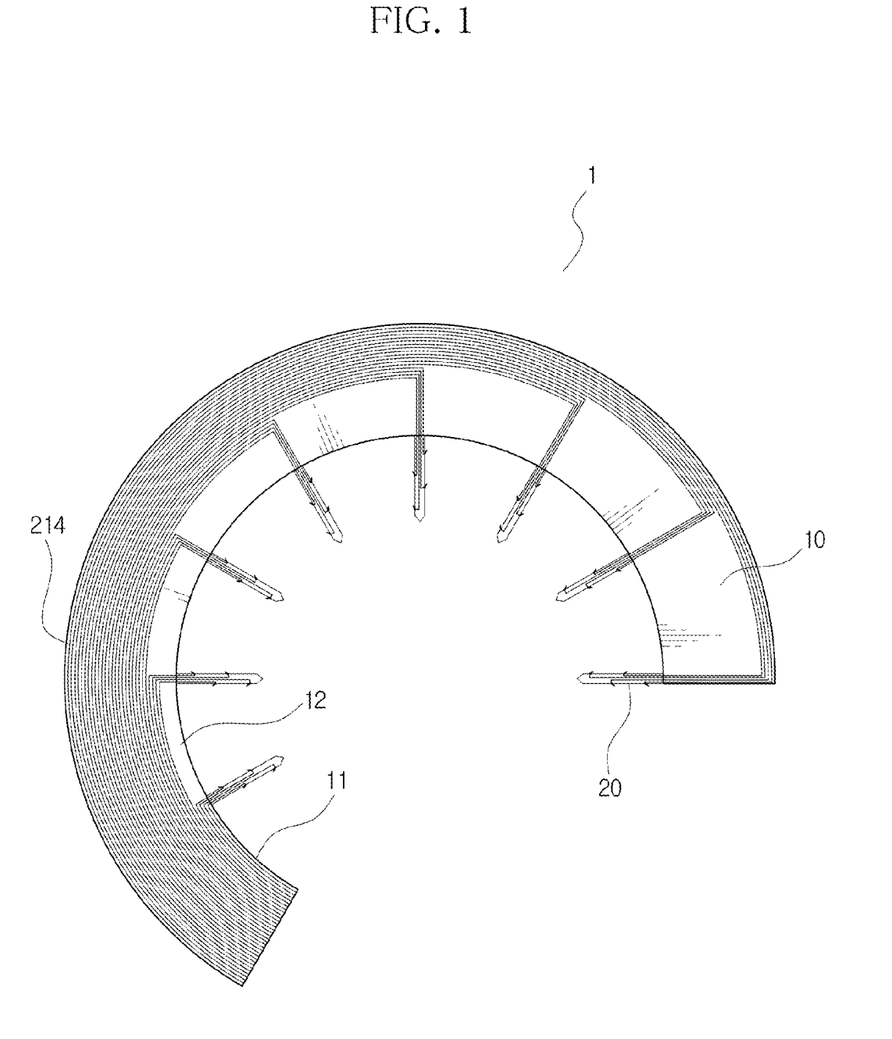
FIG. 1 is a plane view showing a nerve probe array according to an embodiment of the present disclosure.

FIG. 1 is a plane view showing a nerve probe array 1 according to an embodiment of the present disclosure.

As shown in FIG. 1, the nerve probe array 1 includes a connector 10 made of a flexible material and a plurality of probes 20 coupled to the connector 10, each of the plurality of probes having an electrode formed at a body thereof.

The plurality of probes 20 according to this embodiment are disposed with intervals in a length direction of the connector 10.

Figure 2:
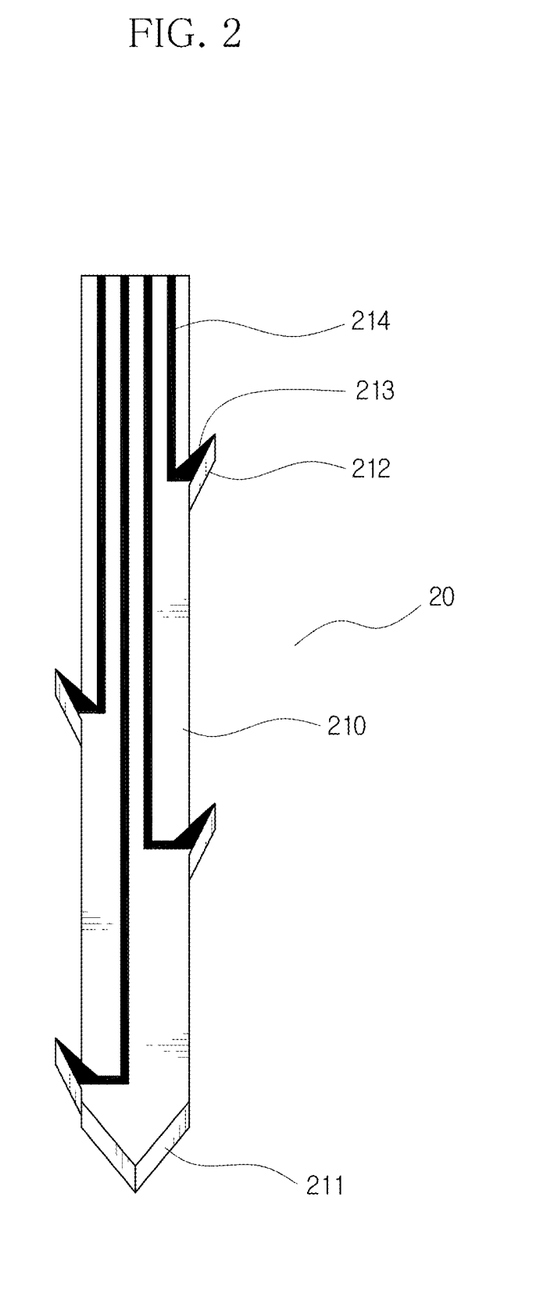
FIG. 2 is an enlarged view showing a probe of the nerve probe array of FIG. 1.

FIG. 2 is an enlarged view showing the probe 20 according to this embodiment.

As shown in FIG. 2, the probe 20 has a body 210 with a long needle shape. According to this embodiment, the probe 20 pierces an outer circumference of a nerve N and is inserted into the nerve N in a length direction thereof, and the body 210 of the probe 20 has a tip 211 with a sharp shape for easy insertion into the nerve N.

In order to minimize that the probe 20 which is being inserted into or has already inserted into the nerve N damages the nerve N, the body 210 of the probe 20 according to this embodiment may be made of a flexible material such as polymer, or a surface of the body 210 may be coated with a flexible material such as polyimide, parylene, silicon, epoxy or the like.

Even when the body 210 of the probe 20 is made of a flexible material, the body 210 may have sufficient rigidity so that the probe 20 may be inserted into the nerve N.

As shown in FIG. 2, a plurality of electrodes 213 are formed at the surface of the body 210 of the probe 20. In this embodiment, four electrodes 213 are formed at a single probe 20.

A cable 214 is electrically connected to each of the four electrodes 213, and the cable 214 may be elongated and electrically connected to a signal processor or a wireless communication device (not shown).

The nerve probe array 1 according to this embodiment may detect a nerve signal at an insertion portion of the probe 20 by using the electrode 213, and when it is intended to check a reaction of a nerve according to an electrical stimulation, the nerve probe array 1 may give an electrical stimulation to the nerve through the electrode 213.

For nerve signal probing or electrical stimulation to a broader region in the nerve N, according to this embodiment, at a single probe 20, the plurality of electrodes 213 are formed at different locations along the length direction of the probe 20.

Accordingly, when the probe 20 is inserted into the nerve, the electrodes 213 make contact with the nerve N at different depths, which may enhance acquisition of nerve signal or selectivity for electrical stimulation portion.

Meanwhile, the nerve probe array 1 according to this embodiment is fixed to the nerve N without any separate support structure, by using a supporting force of the probe 20 against the nerve N.

Therefore, such that the probe 20 inserted into the nerve N is hooked in the nerve and is thus not drawn out in a reverse direction, the probe 20 may include a hook structure to enhance a fixing force of the nerve probe array 1 to the nerve N.

For example, the hook structure may be formed using a so-called "broad head" structure having a wide tip, like an arrowhead or a harpoon, provided at the body 210 of the probe 20.

However, in this case, the wide tip may damage the nerve while being inserted into the nerve, and thus in the probe 20 according to this embodiment, a plurality of sharp protrusions 212 are formed at a linear side of the body 210 to form the hook structure.

An end of the protrusion 212 extends in a direction opposite to the insertion direction of the probe 20. Thus, when the probe 20 is inserted into the nerve, the protrusion 212 does not give resistance, but when the probe 20 receives a force in a reverse direction, the protrusion 212 is hooked in the nerve N to prevent the probe 20 from being easily drawn out.

According to this embodiment, in order to prevent the sharp protrusion 212 from damaging the nerve N, the protrusion 212 has a size smaller than the body 210 of the probe 20. However, in order to enhance the fixing force, a plurality of protrusions 212 are formed at a single probe 20, and the plurality of protrusions 212 are formed at different locations along the length direction of the probe 20.

According to this embodiment, the plurality of protrusions 212 include four protrusions, corresponding to the number of the electrodes 213, and four protrusions 212 are formed to respectively correspond to the locations of four electrodes 213.

Referring to FIG. 1 again, the connector 10 has an arc shape, which is a part of a circle as a whole.

The connector 10 includes a side 12 forming a width of the connector 10 and a side 11 forming a thickness thereof. According to this embodiment, the connector 10 has a thin plate shape (a band shape) whose width is much greater than thickness.

The plurality of probes 20 are formed so that their length direction is approximately in line with the width direction of the connector 10. In addition, the length direction of the plurality of probes 20 is approximately perpendicular to a normal direction of the arc of the connector 10.

According to this embodiment, the connector 10 is made of a polymer material and thus has flexibility.

The cable 214 connected to the electrode 213 of each probe 20 extends along the connector 10. As shown in FIG. 1, four electrodes 214 extending from each probe 20 are elongated in parallel without overlapping each other on the connector 10, till one end of the connector 10. Therefore, in FIG. 1, it may be found that the width formed by cables 214 increases gradually in a counterclockwise direction.

At one end of the connector 10, wireless communication equipment (not shown) or the like may be connected to the cable 214.

Figure 3:
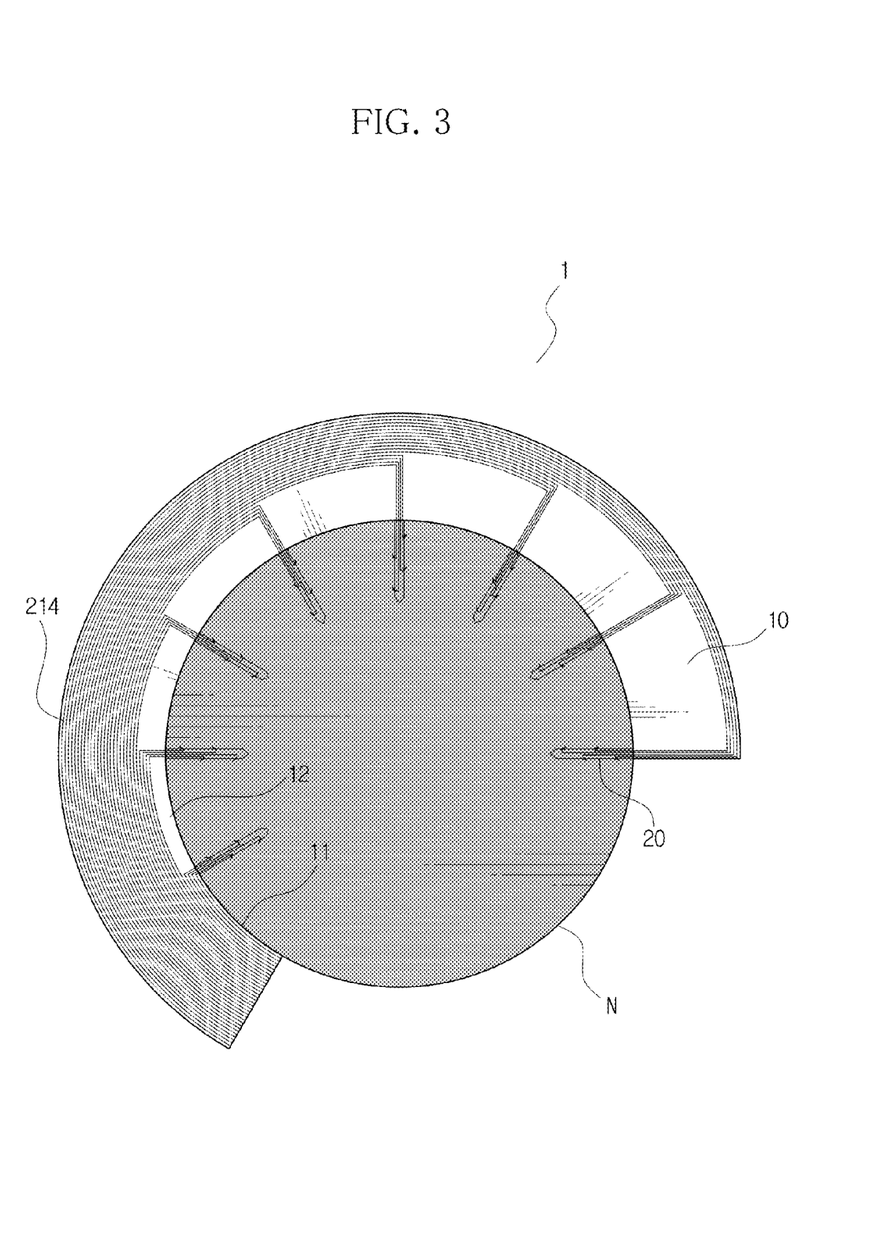
FIG. 3 shows an example in which the nerve probe array of FIG. 1 is connected to a nerve.

FIG. 3 shows an example in which the nerve probe array 1 according to this embodiment is connected to the nerve N. FIG. 3 shows that the nerve N is cut in a direction perpendicular to a length direction thereof.

As shown in FIG. 3, the connector 10 surrounds the outer circumference of the nerve N, and the plurality of probes 20 pierce the outer circumference of the nerve N and are inserted into the nerve.

When the nerve N is observed in a sectional direction in which the nerve N is cut in a direction perpendicular to its length direction, the plurality of probes 20 inserted into the nerve N are arranged radially. Due to this arrangement, it is possible to acquire a plurality of nerve signals or perform electrical stimulation regularly over the entire region of the nerve.

According to this embodiment, the plurality of probes 20 are arranged at regular intervals. Even though the connector 10 is made of a flexible material, since the connector 10 plays a role of fixing the probe 20, if the length of the connector 10 and the intervals of the probes 20 are put into consideration, the probes 20 may be inserted into desired locations in comparison to the case where probes are individually inserted into the nerve. In other words, selectivity to the nerve is enhanced.

Meanwhile, according to this embodiment, the nerve probe array 1 may give a sufficient supporting force to the nerve N due to the structure of the probe 20, and thus it is not needed that the connector 10 is supported by the nerve.

Therefore, as shown in FIG. 3, according to this embodiment, the connector 10 may surround the nerve in a state of erecting so that the side 11 of the connector 10 forming its thickness comes into contact with the outer circumference of the nerve N.

In other words, the connector 10 is used for electrically connecting the probes 20 and positioning the probes 20, and since the connector 10 surrounds the nerve N in an erecting state, its contact area with the outer circumference of the nerve N may be minimized. Therefore, the nerve probe array 1 does not press the nerve and thus does not cause a pain, does not disturb blood circulation through a micro vessel of the nerve eqineurium, and does not disturb movement of substances into or out of the nerve, which may allow the nerve probe array 1 to be transplanted for a long time.

Meanwhile, even though FIG. 1 illustrates that the plurality of probes 20 have the same length, the present disclosure is not limited thereto.

The plurality of probes 20 may include at least probe having a different length from other probes. The plurality of probes 20 may have different lengths from each other, and some probes may have a different length from other probes.

Figure 5:
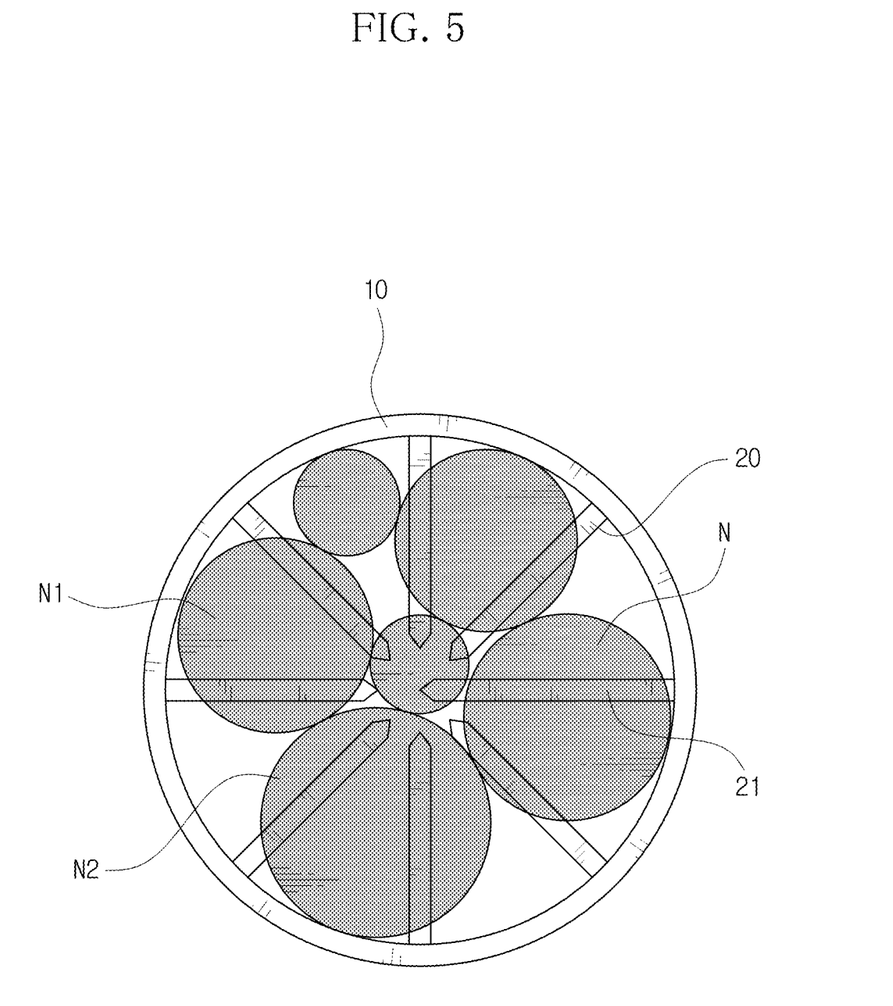
FIG. 5 shows a section of a nerve to which a nerve probe array is connected like FIG. 4.

In an example, at least one of the plurality of probes 20 may be formed to reach a center of the nerve N (see the electrode 21 of FIG. 5).

In this configuration, it is possible to acquire a plurality of nerve signals or perform electrical stimulation regularly over the entire region of the nerve, and the nerve probing or selectivity of stimulation portion may be maximized.

Even though FIG. 3 illustrates that the plurality of probes 20 are radially inserted substantially at the same location in the length direction of the nerve N, the present disclosure is not limited thereto.

If the length, width, thickness and curvature of the connector 10 of the nerve probe array 1 are adjusted, the plurality of probes 20 may be inserted while changing their locations in the length direction of the nerve N.

Figure 4:
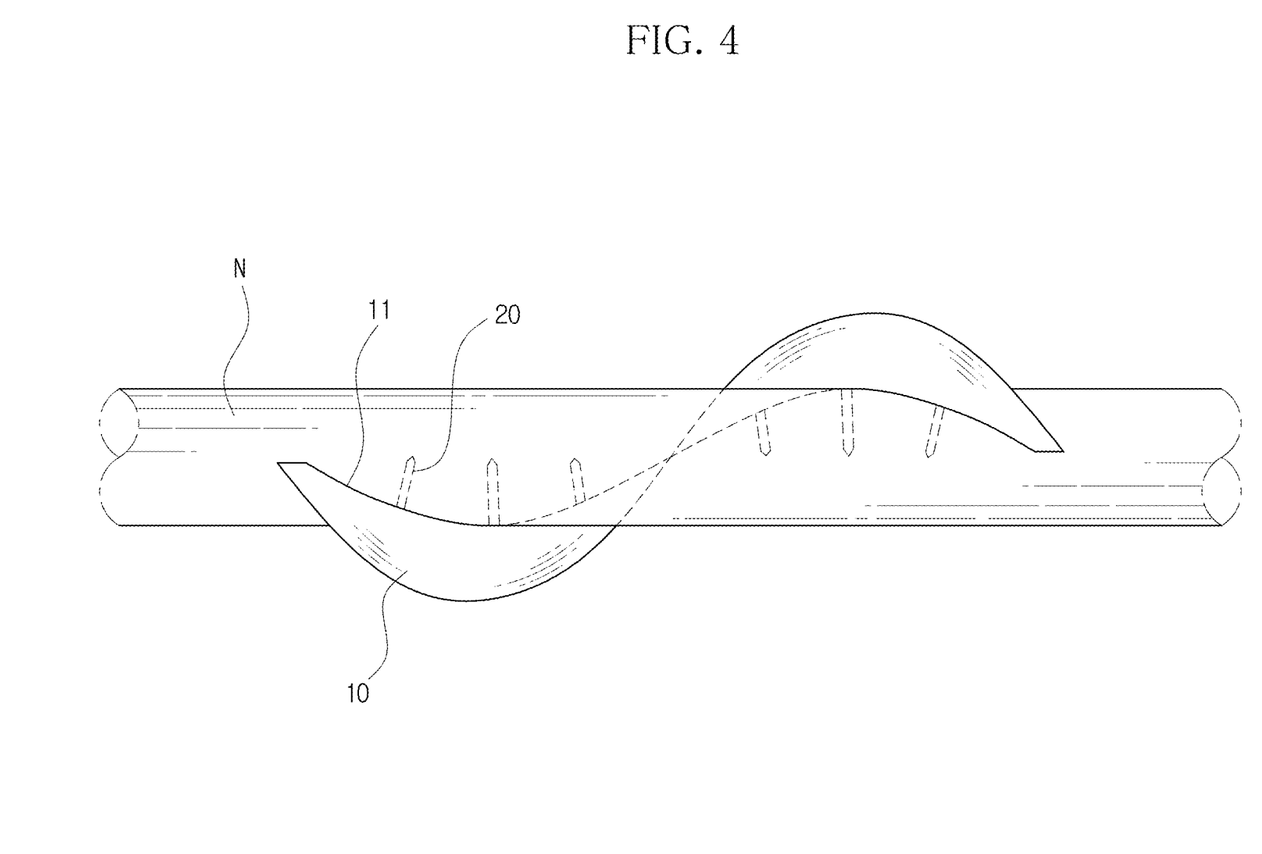
FIG. 4 shows another example in which the nerve probe array of FIG. 1 is connected to a nerve.

FIG. 4 shows another example in which the nerve probe array 1 according to this embodiment is connected to the nerve N. FIG. 5 shows the nerve N to which the nerve probe array 1 is connected as shown in FIG. 4, in a sectional direction.

As shown in FIG. 4, the connector 10 spirally surrounds the outer circumference of the nerve N and is connected to the nerve N.

If the connector 10 surrounds the nerve N in a spiral pattern, the plurality of probes 20 may be inserted into the nerve N at different locations along the length direction of the nerve. Therefore, the plurality of probes 20 do not pierce any one region intensively, thereby minimizing the damage of the nerve N.

Meanwhile, when the connector 10 spirally surrounds the outer circumference of the nerve N, the connector 10 may make at least one turn around the nerve N.

As shown in FIG. 4, even though the connector 10 makes at least one turn around the nerve N, the connector 10 does not perfectly bind the nerve N in a closed loop at any region.

Therefore, it is possible to prevent the connector from pressing the nerve and thus disturbing a flow of blood, different from an existing cuff electrode.

Meanwhile, when the plurality of probes 20 are arranged over the entire length of the connector 10, if the connector 10 makes at least one turn around the nerve N, as shown in FIG. 5, the plurality of probes 20 may be disposed over the entire inside of the nerve N in a radial pattern.

As shown in FIG. 5, the nerve N includes a plurality of nerve bundles N1, N2 therein. Since the plurality of probes 20 are disposed over the entire inside of the nerve N in a spiral pattern, electrodes of high density (great number) may be regularly disposed in the nerve N. Therefore, electrodes may be located at substantially all nerve bundles. Accordingly, accurate nerve signals may be acquired, and nerve probing and stimulation location selectivity may be greatly enhanced.

Meanwhile, similar to the above example, in the example of FIG. 4, the connector 10 also surrounds the nerve in a state of erecting so that the side 11 forming its thickness comes into contact with the outer circumference of the nerve N. Therefore, the contact area with the outer circumference of the nerve N may be minimized.

Figure 6A:
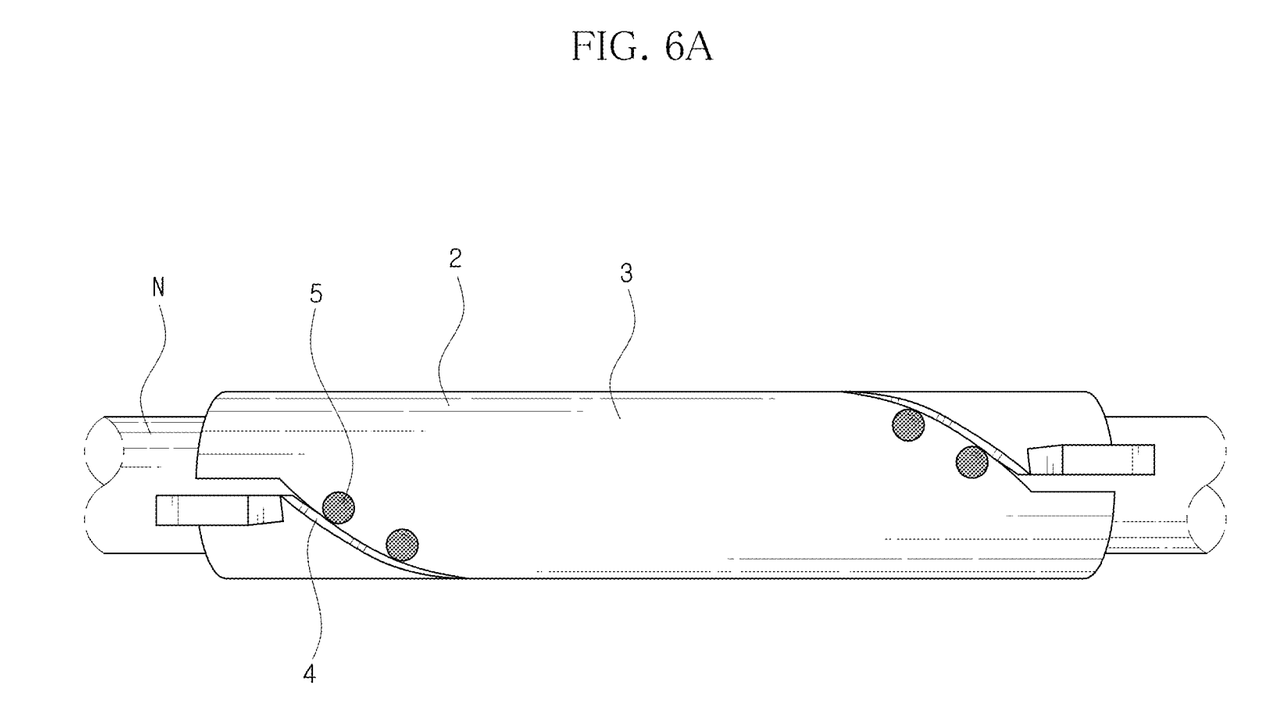
FIGS. 6A and 6B show that the nerve probe array of FIG. 1 is connected to a nerve.
Figure 6B:
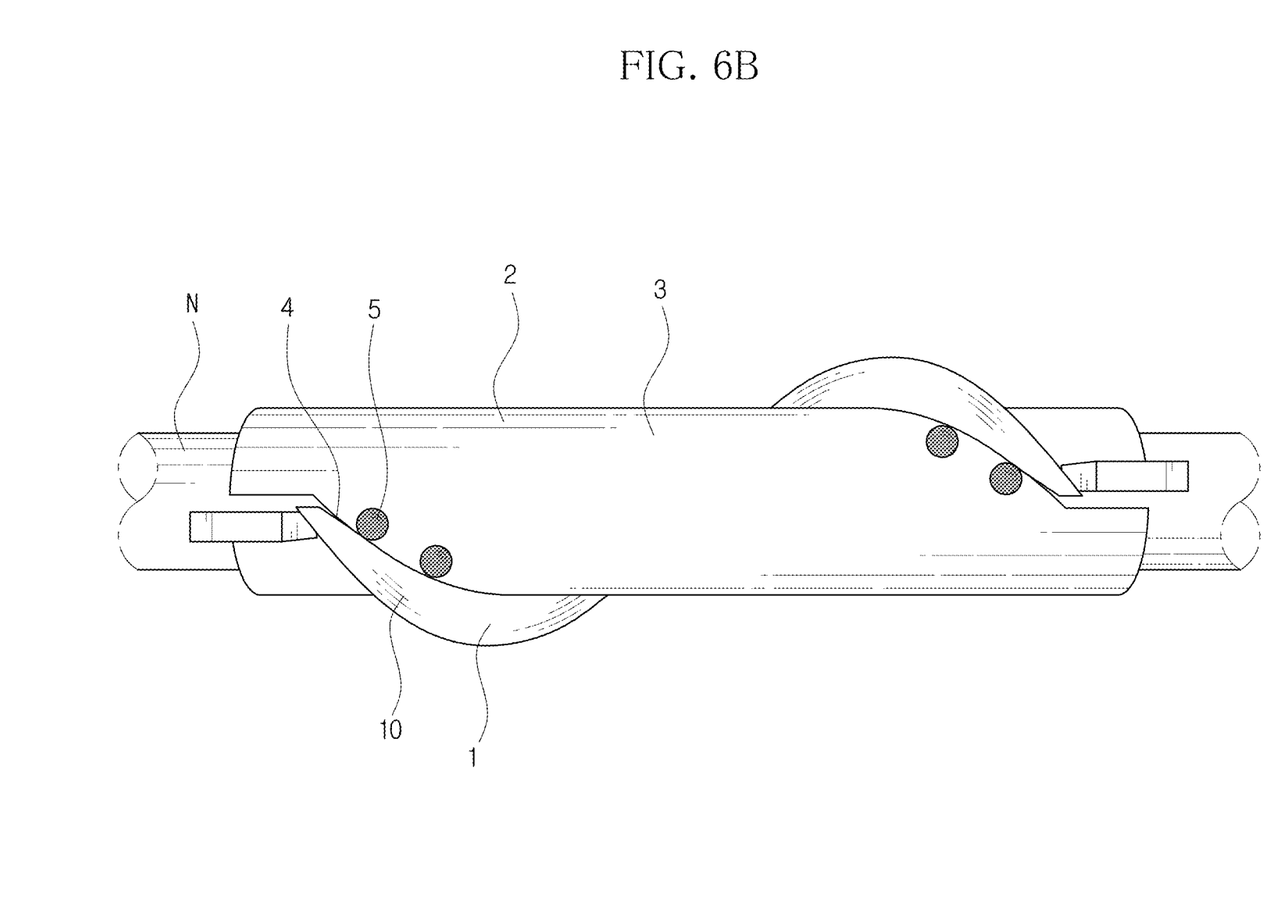

FIGS. 6A and 6B show that the nerve probe array 1 according to this embodiment is connected to the nerve N.

As shown in FIG. 6A, a jig 2 made of a flexible material to connect the nerve probe array 1 is interposed at the periphery of the nerve N in advance.

The jig 2 has a cylindrical body 3, and the body 3 has a thin slit 4 into which the connector 10 and the probe 20 may be inserted. The slit 4 is spirally formed along the length direction of the body 3 and is perfectly opened so that the outer circumference of the nerve N is exposed through the slit 4.

A mark 5 may be formed near the slit 4 to exhibit a location where the probe 20 is to be inserted.

An operator inserts the flexible connector 10 into the slot 4 to wind along the path of the slit 4, and simultaneously drives the probes 20 into the nerve N in order, along a winding direction, while checking a location where the mark 5 is formed.

After this process is completed, the jig 2 is released to be removed from the nerve N, and then, as shown in FIG. 4, the nerve probe array 1 is connected to the nerve N.

Figure 7:
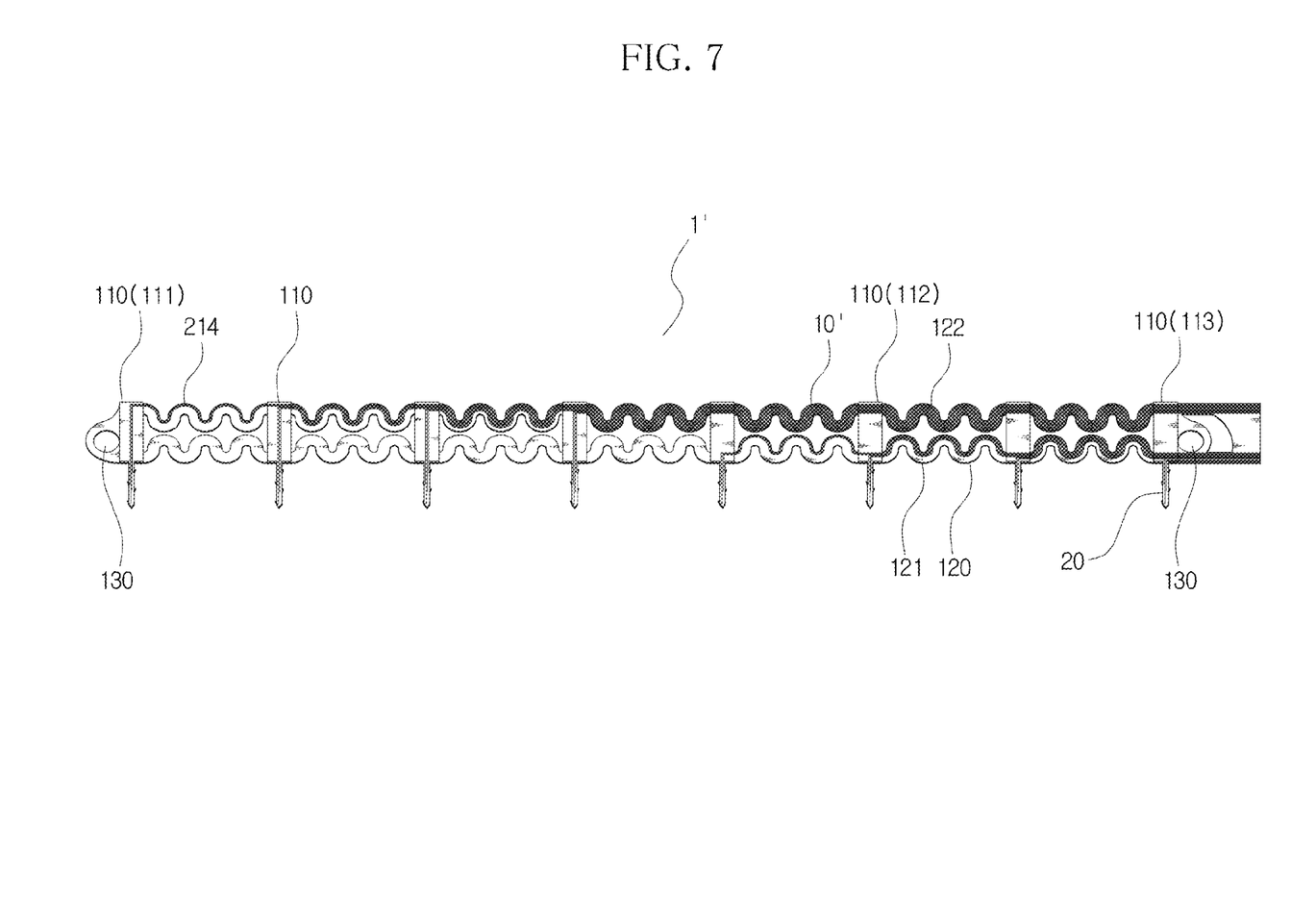
FIG. 7 shows a nerve probe array according to another embodiment of the present disclosure.

FIG. 7 shows a nerve probe array 1' according to another embodiment of the present disclosure.

According to this embodiment, the connector 10' has a linear shape. However, in order to wind the connector 10' around the nerve N in a spiral pattern, the connector 10' is formed to be shrinkable or expandable along its length direction.

As shown in FIG. 7, the connector 10' includes a plurality of fixing portions 110 to which the plurality of probes 20 may be respectively fixed, and an extendable portion 120 for connecting two fixing portions 110 and formed length-adjustably.

The fixing portion 110 has a thin plate shape and may be molded integrally with the body 210 of the probe 20. The probe 20 may be bent or curved as desired with respect to the fixing portion 110.

The extendable portion 120 is made of meander structures 121, 122 which are meanderingly bent to have flexibility and elasticity simultaneously. Two meander structures 121, 122 are formed in parallel to enhance a supporting force to the fixing portion 110 and structurally stabilize the connector 10'.

The cable 214 extending from each probe 20 is elongated along the fixing portion 110 and extends to electronic equipment such as wireless communication equipment through the extendable portion 120.

Four cables 214 extending from each probe 20 are elongated in parallel without overlapping with each other on the connector 10', till an end of the connector 10'.

In FIG. 7, it may be found that the width formed by the cables 214 increases gradually from a leftmost probe 20 to the right.

However, if all cables are accumulatively formed at the extendable portion 120, the extendable portion 120 inevitably has an increased width. Therefore, according to this embodiment, the cable 214 accumulated from the leftmost fixing portion 111 extends to the central fixing portion 112 along the extendable portion 122 at a top side and then extends to the rightmost fixing portion 113, namely to one end of the connector 10', without adding a cable 214.

The cable 214 extending from a probe 20 at a central location extends along the extendable portion 121 at a bottom side to one end of the connector 10'.

According to this embodiment, since the connector 10' has flexibility and elasticity simultaneously, the connector 10' of a linear shape may spirally surround the nerve N, and when being connected to the nerve N, a partial length of the connector 10' may be elongated to adjust locations the probes 20. Therefore, the location of the probe 20 may be adjusted as desired.

Figure 8:
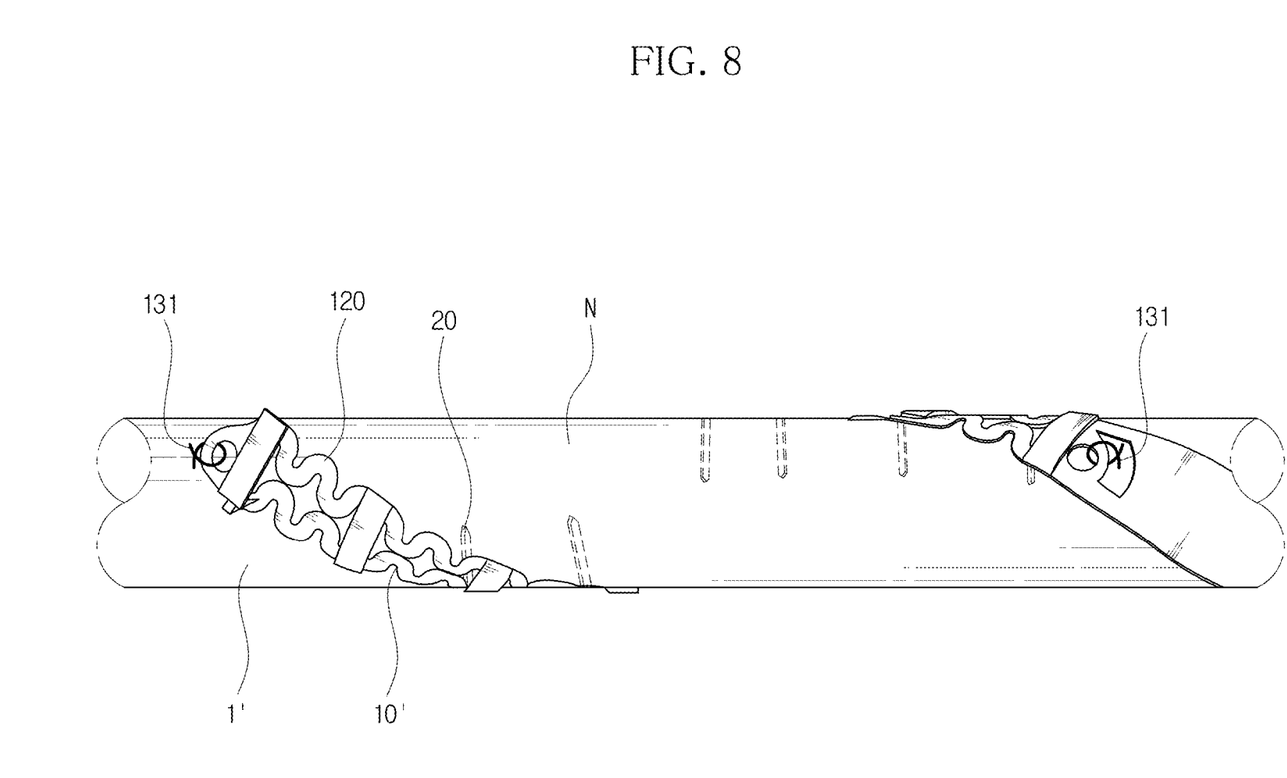
FIG. 8 shows that the nerve probe array of FIG. 7 is connected to a nerve.

FIG. 8 shows that the nerve probe array 1' according to this embodiment is connected to the nerve N.

As shown in FIGS. 7 and 8, for example, loops 130 may be formed at both ends of the connector 1', and a thread 131 may be put into the loops 130 and sewed to the nerve N so that the nerve probe array 1' gives an additional supporting force to the nerve N.

In the embodiment of FIG. 7, the connector has a meander structure, but the present disclosure is not limited thereto.

Figure 9:
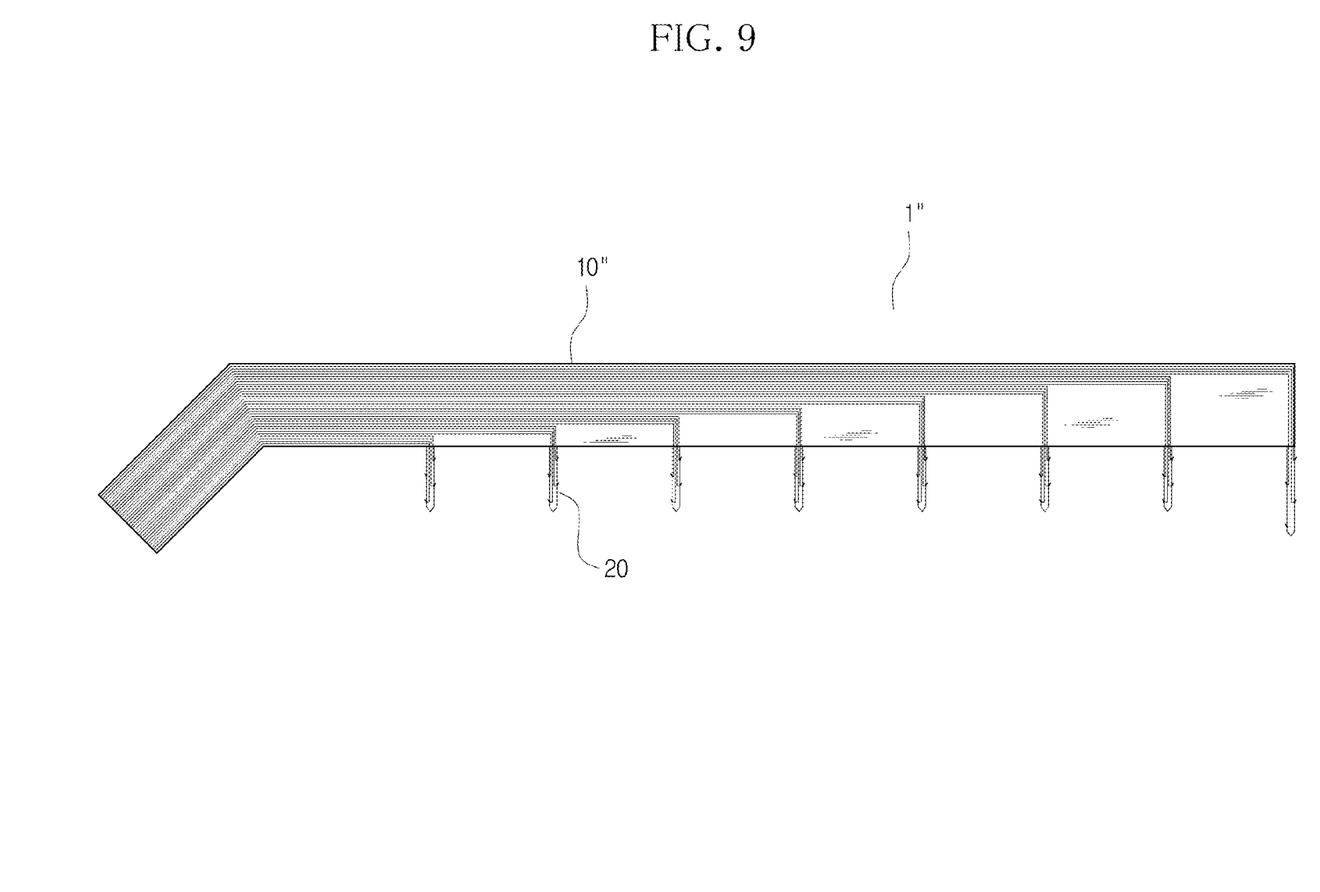
FIG. 9 shows a nerve probe array according to another embodiment of the present disclosure.

FIG. 9 shows a nerve probe array 1" according to another embodiment of the present disclosure.

The nerve probe array 1" according to this embodiment includes a connector 10" having a band shape.

Even though a left portion of the connector 10" is slightly bent so that a user may grip the bent portion when, for example, connecting the nerve probe array 1" to the nerve N, the connector 10" is elongated in a linear shape as a whole.

The connector 10" may be flexibly bent and simultaneously extendable in a length direction thereof. The connector 10" may be made of a silicon material such as PDMS, and various elastomer-type materials may also be used.

If the connector 10" is formed to be length-adjustable, a cable formed thereon may also be formed to be length-adjustable.

For example, the cable may be prepared by mixing conductive nano powder such as carbon nano tube (CNT) or grapheme with PDMS and curing the same, or forming/patterning a metal film on a rubber which has already been stretched to form a wrinkled film cable. In addition, a conductive liquid metal may be put into a fluid channel, which has already been formed in a flexible material, to implement the cable.

Other features of the nerve probe array 1" according to this embodiment are substantially identical to those of the nerve probe array 1 of FIG. 1 and thus not described in detail here.

Figure 10:
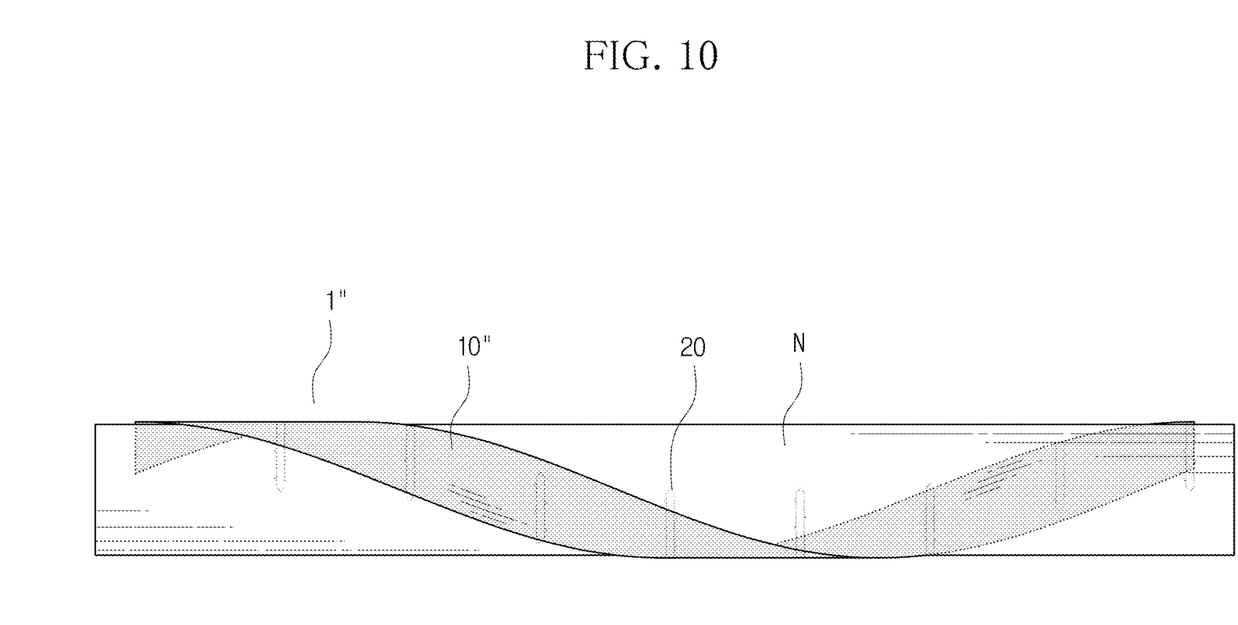
FIG. 10 shows that the nerve probe array of FIG. 9 is connected to a nerve.

FIG. 10 shows that the nerve probe array 1" according to this embodiment is connected to the nerve N.

As shown in FIG. 9, in the nerve probe array 1" according to this embodiment, the connector 10" has a linear shape, and thus the connector 10" may spirally surround the outer circumference of the nerve N more easily in a state where a side of the connector 10" forming its width lies to contact the outer circumference of the nerve N. In this case, the electrode 20 is bent as much as about 90 degrees with respect to the connector 10" and inserted into the nerve N.

However, the nerve probe array 1" is not always connected to the nerve N in the above way, and it will be understood that the connector 10" may also be wound around the nerve N in a standing state so that a side of the connector forming its thickness contacts the outer circumference of the nerve N, by using a tool similar to the jig 2 depicted in FIG. 6 (see FIG. 4).

What is claimed is:

1. A nerve probe array, comprising:
a connector made of a flexible material, comprising a first surface and a second surface, wherein a width of the first surface is greater than a width of the second surface; and
a plurality of probes extending from the second surface, each of the plurality of probes having an electrode formed at a body thereof,
wherein the plurality of probes are arranged with intervals in a length direction of the connector, and
wherein the connector is configured to surround an outer circumference of a nerve, the second surface of the connector is configured to contact with the outer circumference of the nerve, and the plurality of probes are configured to pierce the outer circumference of the nerve and to be inserted into the nerve.

2. The nerve probe array according to claim 1,
wherein the plurality of probes include a probe having a different length from another probe.

3. The nerve probe array according to claim 2,
wherein at least one of the plurality of probes is formed to reach a center of the nerve.

4. The nerve probe array according to claim 1,
wherein the plurality of probes are configured to be arranged radially inserted into the nerve when viewed in a section direction perpendicular to a length direction of the connector.

5. The nerve probe array according to claim 1,
wherein the plurality of probes are arranged at regular intervals.

6. The nerve probe array according to claim 1, wherein the plurality of probes are configured to be inserted into the nerve at different locations along a length direction of the nerve.

7. The nerve probe array according to claim 1,
wherein the connector has an arc shape.

8. The nerve probe array according to claim 1,
wherein the connector has a linear shape and is length-adjustable along the length direction of the connector.

9. The nerve probe array according to claim 8,
wherein the connector includes:
a plurality of fixing portions fixed to the plurality of probes, respectively; and
a length-adjustable extendable portion configured to connect fixing portions adjacent to each other.

10. The nerve probe array according to claim 1,
wherein the plurality of probes are configured to be arranged over the entire length of the connector, when the connector makes at least one turn around the nerve.

11. The nerve probe array according to claim 1,
wherein a plurality of electrodes are configured to be formed at a single probe, and
wherein the plurality of electrodes are configured to be formed at different locations along a length direction of the probe.

12. The nerve probe array according to claim 1,
wherein each of the plurality of probes includes a hook structure so that each of the plurality of probes is hooked at the inside of the nerve and is not drawn in a direction opposite to the insertion direction of each of the plurality of probes into the nerve.

13. The nerve probe array according to claim 12,
wherein the hook structure is a sharp protrusion formed at a side of each of the plurality of probes so that an end of each of the plurality of probes extends in the direction opposite to the insertion direction of each of the plurality of probes into the nerve.

14. The nerve probe array according to claim 13,
wherein a single probe includes a plurality of protrusions,
wherein the plurality of protrusions are configured to be formed at different locations along the length direction of the probe, and
wherein a plurality of electrodes are configured to cover the plurality of protrusions, respectively.

15. The nerve probe array according to claim 1,
wherein the plurality of probes are made of a flexible material or coated with a flexible material at a surface thereof.

* * * * *